US00RE39007E

(19) United States
(12) Reissued Patent
Dattagupta et al.

(10) Patent Number: US RE39,007 E
(45) Date of Reissued Patent: Mar. 7, 2006

(54) ISOTHERMAL STRAND DISPLACEMENT NUCLEIC ACID AMPLIFICATION

(75) Inventors: Nanibhushan Dattagupta, San Diego, CA (US); Paul Douglas Stull, San Diego, CA (US); Marc Spingola, Albuquerque, NM (US); Daniel Louis Kacian, San Diego, CA (US)

(73) Assignee: Gen-Probe Incorporated, San Diego, CA (US)

(21) Appl. No.: 10/164,833

(22) Filed: Jun. 7, 2002

Related U.S. Patent Documents

Reissue of:
(64) Patent No.: 6,087,133
Issued: Jul. 11, 2000
Appl. No.: 08/972,799
Filed: Nov. 18, 1997

U.S. Applications:
(63) Continuation of application No. 08/215,081, filed on Mar. 16, 1994, now abandoned.

(51) Int. Cl.
*C12P 19/34* (2006.01)
*C12Q 1/68* (2006.01)
*C07H 21/02* (2006.01)
*C07H 21/04* (2006.01)

(52) U.S. Cl. ..... 435/91.1; 435/91.2; 435/6; 536/23.1; 536/24.33

(58) Field of Classification Search ..... 435/6, 435/91.1, 91.2; 536/23.1, 24.3, 24.33
See application file for complete search history.

(56) References Cited

U.S. PATENT DOCUMENTS

| | | | | |
|---|---|---|---|---|
| 4,683,195 A | * | 7/1987 | Mullis et al. | |
| 4,683,202 A | * | 7/1987 | Mullis | |
| 4,786,600 A | * | 11/1988 | Kramer et al. | |
| 4,800,159 A | * | 1/1989 | Mullis et al. | |
| 5,043,272 A | * | 8/1991 | Hartley | |
| 5,108,892 A | * | 4/1992 | Burke et al. | |
| 5,223,414 A | * | 6/1993 | Zarling et al. | |
| 5,256,775 A | * | 10/1993 | Froehler | |
| 5,270,184 A | * | 12/1993 | Walker et al. | |
| 5,384,242 A | * | 1/1995 | Oakes | |
| 5,786,183 A | | 7/1998 | Ryder et al. | |
| 6,214,587 B1 | * | 4/2001 | Dattagupta et al. | 435/91.2 |

FOREIGN PATENT DOCUMENTS

| | | | |
|---|---|---|---|
| EP | 0200362 | * | 3/1986 |
| EP | 0300796 | * | 7/1988 |
| EP | 0329822 | * | 8/1988 |
| EP | 0320308 | * | 12/1988 |
| EP | 0395398 | * | 4/1990 |
| EP | 0408295 | * | 7/1990 |
| EP | 0427073 | | 10/1990 |
| EP | 0427074 | | 10/1990 |
| EP | 0497272 | | 1/1992 |
| EP | 0500224 | | 1/1992 |
| EP | 0543612 | | 5/1993 |
| WO | 8706270 | | 4/1986 |
| WO | 8810315 | | 6/1987 |
| WO | 8901050 | | 7/1987 |
| WO | 9102/818 | * | 8/1989 |
| WO | 9102818 | | 8/1989 |
| WO | 9110746 | | 1/1990 |
| WO | WO 94/03635 A1 | | 2/1994 |

OTHER PUBLICATIONS

Feinburg & Vogelstein, "A Technique for Radiolabeling DNA Restriction Endonuclease Fragments to High Specific Activity," Analytical Biochemistry, 132:6–13 (1983).*
Murakawa et al., "Direct detection of HIV–1 RNA from AIDS and ARC patient samples," DNA, 7:287–295 (1988).*
Shaw et al., "Modified deoxyoligonucleotides stable to exonuclease degradation in serum," Nucleic Acids Research, 19(4):747–750 (1991).*
Titeeva et al., "Complexing of Single–Stranded Phage DNA with Synthetic Oligodeoxynucleotides and the Reaction of the Complexes with DNA Polymerase and Restriction Endonucleases," Bioorganicheskaya Khimiya, 12(11):1484–1491 (1986). English Translation.
Walker et al., "Isothermal in vitro amplification of DNA by a restriction enzyme/DNA polymerase system," Proc. Natl. Acad. Sci. U.S.A., 89:392–396 (1992).
Walker et al., "Strand displacement amplification—an isothermal, in vitro DNA amplification technique," Nucleic Acids Research, 20:1691–1696 (1992).
Chien et al., "DNA polymerase from the extreme thermophile *Thermus aquaticus*," J. Bacteriology, 127:1550–1557 (1976).
Kaledin et al., "Isolation and properties of DNA polymerase from extremely thermophilic bacterium *Thermus aquaticus* YT1," Biokhimiya, (45)4:644–651 (1980). English translation.

* cited by examiner

*Primary Examiner*—Jehanne Sitton
(74) *Attorney, Agent, or Firm*—Charles B. Cappellari; Carlos A. Fisher

(57) ABSTRACT

Methods for amplifying target nucleic acid sequences using a nucleic acid polymerase lacking 5' exonuclease activity and a set of oligonucleotide primers. Preferably, a primer array is used. The primer array contains two sets of primers. One set contains at least two complementary primers. The other set contains at least two sense primers. Using the described methods amplification can be carried out under essentially constant environmental conditions without the requirement for exonuclease activity or restriction endonuclease activity.

42 Claims, 1 Drawing Sheet

ISOTHERMAL STRAND DISPLACEMENT NUCLEIC ACID AMPLIFICATION

Matter enclosed in heavy brackets [ ] appears in the original patent but forms no part of this reissue specification; matter printed in italics indicates the additions made by reissue.

This application *is a reissue application of U.S. Pat. No. 6,087,133, which issued from application Ser. No. 08/972, 799, which* is a continuation of application Ser. No. 08/215, 081, filed Mar. 16, 1994, now abandoned. *Application 10/165,281 is a reissue application of U.S. Patent No. 6,214,587, which issued from application Ser. No. 09/506, 282, which is a continuation of application Ser. No. 08/972, 799, now U.S. Patent 6,087,133, of which this application is a reissue application.*

FIELD OF INVENTION

This invention relates to methods for amplifying nucleic acid sequences without thermal cycling.

BACKGROUND OF THE INVENTION

This invention concerns diagnostic procedures and techniques for amplifying a nucleic acid sequence. The detection and quantitation of a specific nucleic acid sequence (i.e., a target sequence) is an increasingly important technique having numerous applications including identifying and classifying microorganisms, diagnosing infectious diseases, detecting and characterizing genetic abnormalities, identifying genetic changes associated with cancer, studying genetic susceptibility to disease, measuring the response to various types of treatment, identifying criminal suspects, and resolving paternity disputes.

A common method for detecting and quantitating target nucleic acid sequences is nucleic acid hybridization. Nucleic acid hybridization, typically, uses a labeled nucleic acid probe having a nucleic acid sequence complementary to the target sequence. The probe is mixed with a sample suspected of containing the target sequence under conditions suitable for hybrid formation. The probe then hybridizes to the target sequence present in the sample. Hybridization can be detected by various techniques well known in the art. These techniques include selectively degrading the label present on unhybridized probe and then measuring the amount of label associated with the remaining hybridized probe (Arnold et al., PCT US88/02746).

Numerous methods are available for amplifying nucleic acid strands (i.e., nucleic acid polymers) to increase the amount of target sequence. These methods use the nucleic acid strand containing the target sequence as a template to produce a complementary nucleic acid strand containing the target sequence. Such methods include the polymerase chain reaction method (PCR), as described by Mullis et al., (See U.S. Pat. Nos. 4,683,195, 4,683,202, and 4,800,159 and European Patent Application Nos. 863022-98.4, 86302299.2, and 87300203.4, and Methods in Enzymology, Volume 155, 1987, pp. 335–350). PCR involves the use of a pair of specific oligonucleotides as primers for the two complementary strands of the double-stranded DNA containing the target sequence. The primers are chosen to hybridize at the ends of each of the complementary target strands, 3' of the target sequence. Template-dependent DNA synthesis, on each strand, can then be catalyzed using a thermostable DNA polymerase in the presence of the appropriate reagents. A thermal cycling process is required to form specific hybrids prior to synthesis and then denature the double stranded nucleic acid formed by synthesis. Repeating the cycling process geometrically amplifies the target sequence. A PCR method may also be used with an RNA target using RNA-dependent DNA polymerase to create a DNA template.

The PCR method has been coupled to RNA transcription by incorporating a promoter sequence into one of the primers used in the PCR reaction and then, after amplification by the PCR method, using the double-stranded DNA as a template for the transcription of single-stranded RNA (See, e.g., Murakawa et al., DNA 7:287–295 (1988)). Other amplification methods use multiple cycles of RNA-directed DNA synthesis and transcription to amplify DNA or RNA targets (See, e.g., Burg et al., WO 89/1050; Gingeras et al., WO 88/10315 (sometimes called transcription amplification system or TAS); Kacian and Fultz, EPO Application No. 89313154; Davey and Malek, EPO Application No. 88113948.9; Malek et al., W091/02818). Urdea, W091/10746, describe a method that achieves signal amplification using a T7 promoter sequence.

The ligase chain reaction (LCR) is described in European Patent Publication 320,308. This method requires at least four separate oligonucleotides, two of which hybridize to the same nucleic acid template so their respective 3' and 5' ends are juxtaposed for ligation. The hybridized oligonucleotides are then ligated forming a complementary strand on the nucleic acid template. The double-stranded nucleic acid is then denatured, and the third and fourth oligonucleotides are hybridized with the first and second oligonucleotides that were joined together. The third and fourth oligonucleotides are then ligated together. Amplification is achieved by further cycles of hybridization, ligation, and denaturation.

The Qβ replicase (QβR) method described in PCT Publication No. 87-06270 and U.S. Pat. No. 4,786,600 uses a specific RNA probe which is capable of specific transcrip- tion by a replicase enzyme. The method requires the design and synthesis of RNA probes with replicase initiation sites.

Amplification methods using palindromic probes are described in EPO Publication Nos. 0427073A and 0427074A. The palindromic probe forms a hairpin with a nucleic acid target sequence. The probe contains a functional promoter located in the hairpin region from which RNA transcripts are produced.

Walker et al., Proc. Natl. Acad. Sci. U.S.A., 89:392–396 (Jan. 1992), Walker et al., Nucl. Acids Res. 20:1691–1696 (1992), European Patent Application No. EP 0 497 272 A1, and European Patent Application No. EP 0 500 224 A2, describe an oligonucleotide-driven amplification method using a restriction endonuclease. The restriction endonuclease nicks the DNA/DNA complex to enable an extension reaction and, therefore, amplification.

Becker, et al., EPO Application No. 88306717.5, describe an amplification method in which a primer is hybridized to a nucleic acid sequence and the resulting duplex cleaved prior to the extension reaction and amplification.

Noonan, K. E. et al., Nucl. Acids Res. 16, 10366 (1988), describe using random hexamers to prime reverse transcriptase in a random, nonspecific manner for the synthesis of cDNA from mRNA. Amplification of the desired target is accomplished with PCR.

Feinberg, A. P. et al., Anal. Biochem. 132, 6 (1983), and Liang, W. et al., Nucl. Acids Res. 16,3579 (1988), describe the synthesis of DNA strands complementary to a DNA template by combining single-stranded DNA with random hexanucleotide primers, deoxynucleoside triphosphates, buffer, the Klenow fragment of E. coli DNA polymerase 1, and a labeled deoxynucleoside triphosphate.

A related process, known as Random Priming Amplification (RPA) for amplifying nucleic acid is described by Hartley, U.S. Pat. No. 5,043,272. According to Hartley, at columns 2–3, lines 63–2:

> The process includes the steps of priming single-stranded template nucleic acid strands with an excess of random oligonucleotide primers and incubating the single-stranded template nucleic acid strands and excess random oligonucleotide primers in the presence of excess amounts of an inducing agent, a strand displacement agent, and nucleoside triphosphate substrates to randomly amplify nucleic acid strands.

SUMMARY OF THE INVENTION

The present invention features methods for amplifying target nucleic acid sequences using a nucleic acid polymerase lacking 5' exonuclease activity and oligonucleotide primers. Alternatively, the method of the present invention may be performed using a nucleic acid polymerase having 5' exonuclease activity if the oligonucleotide primers have a 5' modification which prevents or reduces nucleolytic digestion of the primers. Preferably, amplification is carried out using a primer array comprising two sets of primers. One set contains at least two primers complementary to the target nucleic acid. The other set contains at least two primers of the same sense as the target nucleic acid. Using the described methods amplification can be carried out under essentially constant environmental conditions without the requirement for exonuclease activity or restriction endonuclease activity. Preferably, amplification is carried out using a DNA template, and a DNA polymerase such as a modified Bacillus stearothermophilus (Bst) DNA polymerase which lacks 5' exonuclease activity.

The oligonucleotide members of each primer set are used as initiation points for template-dependent synthesis of a complementary nucleic acid strand, and to enhance displacement of the synthesized complementary strand. Thus, strand displacement and nucleic acid synthesis are carried out in one step. This is a surprising finding, and Applicant is unclear of the exact mechanism by which the procedure operates.

Only one set of primers is believed necessary to effectuate strand displacement and nucleic acid synthesis. A primer array is preferably used to amplify both the initial template and its complement to exponentially amplify a target sequence.

Preferably, the nucleic acid polymerase lacks 5' exonuclease activity, and the procedure is performed at higher temperatures than those at which enzymes such as the Klenow fragment of E. coli DNA polymerase I are optimally active. The reaction is more efficient at 43° C. than at 37° C. Optimal efficiency is obtained at temperatures between 50° C. and 70° C. The method is preferably used on DNA. An RNA target sequence is preferably amplified by first creating a DNA copy using, for example, reverse transcriptase. The DNA copy is then amplified by the methods described herein.

However, the present invention should be able to directly amplify an RNA sequence using an enzyme able to synthesize an RNA complementary strand on an RNA template. Such an enzyme preferably lacks 5' exonuclease activity. For example, QB replicase used in conjunction with manganese should be suitable for this purpose.

Thus, in a first aspect, the invention features a method for amplifying a target nucleic acid sequence by contacting a nucleic acid strand containing the target sequence with a nucleic acid polymerase lacking 5' exonuclease activity (5'-exo-minus polymerase), four different nucleotides, and at least two complementary oligonucleotide primers. Preferably, four different deoxynucleotides and/or three of more primers are used. The amplification is carried out under primer extension conditions at essentially constant temperature.

In related aspects amplification is carried out using a nucleic acid polymerase that has 5' exonuclease activity but under conditions wherein such activity is inhibited, and amplification is carried out using at least two complementary oligonucleotide primers in the absence of a restriction endonuclease active on the products of any extension reaction of said contacting step.

In another related aspect, the invention features a method for amplifying a target nucleic acid sequence by contacting a nucleic acid strand containing the target sequence with a nucleic acid polymerase lacking 5' exonuclease activity (5'-exo-minus polymerase), four different nucleotides, at least two complementary oligonucleotide primers, and at least two sense primers. The amplification is carried out under primer extension conditions at essentially constant temperature. Preferably, the total number of complementary primers and sense primers is more than 5.

The nucleic acid strand present prior to amplification serves as an initial nucleic acid template for the synthesis of a complementary strand containing the target sequence. The complementary strand can act as a nucleic acid template to produce strands analogous to the initial nucleic acid template. The analogous strands can act as nucleic acid templates. Thus, the resulting amplification of target sequence is geometric.

Primer extension conditions refer to conditions wherein template-dependent amplification initiated at an oligonucleotide primer can occur. Such conditions generally include provision of an appropriate buffer and, optionally, other chemicals that may stabilize the polymerase, or enhance primer extension reactions.

"Template" refers to a nucleic acid strand, such as DNA or RNA, which can serve as a substrate for the synthesis of a complementary nucleic acid strand.

A "target sequence" refers to a specific nucleic acid sequence contained on a single strand of an oligonucleotide or nucleic acid molecule, or the nucleic acid sequence complementary thereto.

A "complementary primer" refers to an oligonucleotide primer having a nucleic acid sequence complementary to a nucleic acid sequence present on the nucleic acid template. Complementary primers are designed to be complementary to nucleic acid sequences, on the nucleic acid template, in regions 3' to the target sequence.

By "complementary" is meant that the oligonucleotide primer can hybridize to a region of the nucleic acid template under the conditions of the contacting step so it can be extended in a primer extension reaction. Generally, such oligonucleotides have a region of complementarity to the template of between 15 and 100 bases, preferably between about 20 and 50 bases. Preferably the region of complementarity is 100% complementary. That is, each nucleotide in the primer complementary region can hydrogen bond with a nucleotide present on the single-stranded template.

However, those of ordinary skill in the art will recognize that primers having a complementary region less than 100% complementary to the template will operate in this method. Generally, such complementarity can be as few as 15 out of 18 contiguous bases.

A "sense primer" refers to an oligonucleotide analogous to a nucleic acid sequence present on the nucleic acid template. A sense primer is designed to be analogous to a region on the template 5' of the target sequence.

By "analogous" is meant that the oligonucleotide has essentially the same, or equivalent, nucleotide sequence as that in the nucleic acid template. Thus, for example, the oligonucleotide may contain uracil in place of a thymine present in the nucleic acid template. The analogous oligonucleotides are preferably sufficiently duplicative of the template so they can act as a complementary primer when hybridized to a nucleic acid that is complementary to the nucleic acid template, under primer extension conditions.

Thus, reference to complementary primers and sense primers is made with respect to a particular template. The same primer can act as a complementary primer or a sense primer depending upon whether it is analogous to, or complementary to, a particular template.

Primer-dependent amplification of a target sequence present on a nucleic acid template is achieved in the contacting step. The degree of amplification has been found to increase with increasing numbers of primers. Examples are provided below using as many as 13 primers (seven sense and six complementary), and as few as two primers (two complementary primers). These examples illustrate the ability of primers to cause amplification and are not intended to limit the invention. Preferably, the complementary primer set and the sense primer set each contain more than two primers. In preferred embodiments, at least 4 sense primers and 4 complementary primers are used; at least 7 sense primers and 7 complementary primers are used; and at least 10 sense primers and 10 complementary primers are used.

As illustrated in the FIGURE, a set of complementary primers comprise oligonucleotides complementary to the template in regions 3' of the target sequence. A set of sense primers comprise oligonucleotides analogous to the template in regions 5' of the target sequence on the same strand. The oligonucleotides are selected so a primer extension reaction is initiated on the nucleic acid template at a site different from the other oligonucleotide primers, and preferably at a site distinct from the region in which the other oligonucleotide primers form base pairs. Preferably, the oligonucleotides in a primer set are separated at their closest 5' and 3' ends from one another by 1 to 200 bases, and more preferably, are separated by between 1 and 10 bases.

By "four different nucleotides" is meant that adenosine (A), guanosine (G), cytidine (C) thymidine (T), and uridine (U) triphosphates, or an equivalent nucleotide which can be substituted for an adenosine, guanosine, cytidine, thymidine, or uridine nucleotide triphosphate, are present as substrates for nucleic acid synthesis. Preferably, deoxynucleotides are used.

By "amplifying" is meant increasing the number of target sequences.

By "contacting" is meant that the nucleic acid template, the nucleic acid polymerase, the four different nucleotides, and the oligonucleotide primer array are brought together under primer extension conditions.

By "essentially constant temperature" is meant that the user makes no attempt to raise or lower the temperature in any profound manner as is used in the polymerase chain reaction to alternatively carry out primer extension and denature the extension products. Thus, the temperature is kept below the temperature at which the template:primer extension product duplex dissociates. Preferably, the temperature is kept below 90° C. More preferably, the reaction temperature is maintained at about the optimum temperature for the reaction. Generally, such an optimum is between 42° C. and 60° C. and is preferably between 50° C. and 70° C.

In preferred embodiments, the conditions include the provision of DMSO; the essentially constant temperature is at least 43° C., and most preferably between 50° C. and 70° C.; the conditions include a strand separation agent such as a helicase, at least one nucleotide triphosphate, selected from a protein having an activity corresponding to the RecA protein of E. coli, or a single-stranded nucleic acid binding protein; the DNA polymerase is a 5' exominus Bst DNA polymerase I or a modified Taq DNA polymerase; and at least one of the oligonucleotide primers includes a 5' non-complementary region. The RecA protein is not necessary for amplification in this invention, but rather can be used to enhance such amplification.

By "5' exonuclease minus" is meant that the nucleic acid polymerase has essentially no 5' exonuclease activity associated with it, or has been treated such that the exonuclease activity is reduced or inactive. The preferred nucleic acid polymerase is a 5' exonuclease minus DNA polymerase. Examples of DNA polymerases having no 5' exonuclease activity include a proteolytic fragment of DNA polymerase I from Bacillus stearothermophilus, and the DNA polymerase from Thermus aquaticus having its domain encoding 5' exonuclease activity removed as described by Barnes, "Thermostable DNA Polymerase," PCT/US91/07084. The exonuclease minus polymerase of the Klenow fragment described by Walker, supra, may also be used.

In a related aspect, the invention features a method and means for amplifying a nucleic acid target sequence by the step of contacting the nucleic acid containing the target sequence with a nucleic acid polymerase that may have 5' exonuclease activity but under conditions wherein such activity is inhibited. Specifically, at least one oligonucleotide primer is modified to be resistant to nucleolytic degradation by any 5'-exonuclease present in the nucleic acid polymerase. Preferably, at least one complementary and one sense primer is modified to be resistant to 5'-exonuclease activity. More preferably all primers are resistant to such degradation.

Thus in this aspect, the contacting step contains four different nucleotide triphosphates, at least two different complementary oligonucleotide primers and at least two different oligonucleotide sense primers, one or more of which are blocked. The reaction is carried out under oligonucleotide primer extension conditions at essentially constant temperature in the absence of a restriction endonuclease active on the products of any extension reaction of the contacting step.

In related aspects, amplification is carried out using a primer array and either a 5'-exo-minus DNA polymerase or a DNA polymerase containing 5' exonuclease activity used in conjunction with a 5'-exonuclease resistant primers.

As noted above, the present invention does not require a restriction endonuclease active on the products of any primer extension reaction resulting from the contacting step. In contrast to the description in Walker, supra, where the presence of such activity appears to be essential, Applicant has surprisingly found that no restriction enzyme is needed to create a single-stranded region which can be used by oligonucleotide primers in the contacting step.

Thus, in another aspect the invention features a method for amplifying a target nucleic acid sequence by contacting a nucleic acid strand containing the target sequence with a nucleic acid polymerase lacking 5' exonuclease activity, four different nucleotides, a set of at least two complementary oligonucleotide primers, and a set of at least two sense primers. The amplification is carried out under primer extension conditions at essentially constant temperature in the absence of any restriction endonuclease active on the products of any extension reaction. The amplification is preferably carried out as described above.

In related aspects amplification is performed without any restriction endonuclease active on the products of any extension reaction using a nucleic acid polymerase containing 5' exonuclease activity in conjunction with a 5'-exonuclease-resistant primer; or a single stranded DNA substrate and either a 5'-exo-minus DNA polymerase or a DNA polymerase containing 5' exonuclease activity used in conjunction with a 5'-exonuclease-resistant primer. Such amplifications are preferably carried out as described above.

In this invention, amplification can be allowed to proceed for any desired length of time with product accumulating as a result of amplification of the target sequence. Where the target sequence is of analytical interest, high sensitivity detection of the target sequence can be accomplished by amplifying the target in the manner of the present invention and then detecting the accumulated amplification product using techniques known in the art.

The present amplification method provides a number of significant benefits. The present method requires only a nucleic acid polymerase as opposed to several different enzymes, amplification of a specific nucleic acid sequence is more efficient and requires less reagent than a random amplification process, and there is no need for time-consuming and cumbersome thermal cycling.

Other features and advantages of the invention will be apparent from the following description of the preferred embodiments, and from the claims.

BRIEF DESCRIPTION OF THE DRAWING

The FIGURE is an example illustrating the location of primers relative to each other and a target sequence. The FIGURE shows four complementary primers ("−"), four sense ("+") primers, and the location of a target sequence (rectangular box).

DESCRIPTION OF THE PREFERRED EMBODIMENTS

Figure 1:
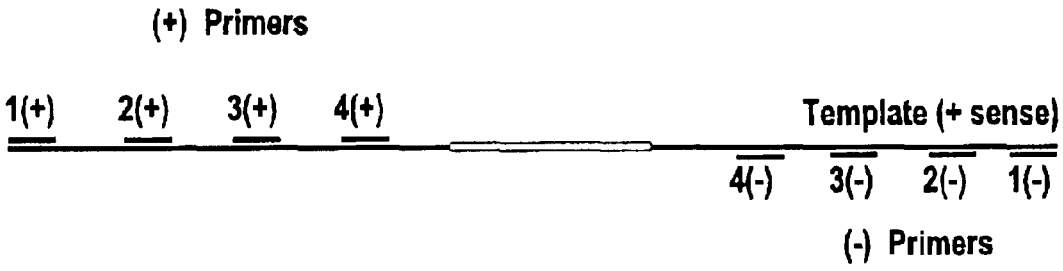

The present invention features methods for amplifying a target nucleic acid sequence present in a nucleic acid, or a mixture of nucleic acids, by a process which includes synthesis of nucleic acid sequences in a specifically-primed template-dependent manner with a nucleic acid polymerase (e.g., a DNA polymerase) and oligonucleotides primers, preferably, a primer array. A primer array is made up of a set of complementary primers and a set of sense primers. Nucleic acid synthesis is initiated at a complementary primer. Without being bound to any theory, it is believed that primer-dependent synthesis occurring from one primer causes strand displacement of a strand synthesized from a different primer.

Thus, the amplification can be performed without modifying reaction conditions such as temperature, pH, or ionic strength during the amplification procedure to alternatively carry out amplification and denature the double-stranded nucleic acid produced during amplification. In addition, amplification can be performed without producing single-stranded substrates using enzymes having exonuclease activity or restriction endonuclease activity.

The process includes the step of priming template nucleic acid strands with a primer array of sequence-specific oligonucleotide primers, for each different target sequence to be amplified. The mixture is incubated in the presence of a nucleic acid polymerase, nucleotide substrates, and any necessary co-factors needed to amplify the target nucleic acid sequence.

As a result of the methods described herein, multiple rounds of template-dependent nucleic acid synthesis occur, concomitant with strand displacement of the previously synthesized strand. The displaced strand can act as a template in conjunction with the "sense primers", which now act as complementary primers.

Oligonucleotide Primer

The term "primer" refers to an oligonucleotide (whether occurring naturally as in a purified restriction digest, or produced synthetically) which can act as a point of initiation of nucleic acid synthesis on a nucleic acid template when contacted under primer extension conditions. Appropriate conditions include the presence of nucleotide substrates, a nucleic acid polymerase (e.g., a 5'-exo-minus DNA polymerase), essentially constant temperature and a suitable pH. The nucleic acid synthesis occurs in a template-dependent manner wherein the sequence of the newly synthesized nucleic acid strand is complementary to the sequence of the nucleic acid template.

Hybridization of the primer to the template may be inhibited by primer secondary structure arising from intramolecular or intermolecular hydrogen bonding. Thus the primer preferably lacks secondary structure and is single-stranded. A primer having a secondary structure which would inhibit hybridization to the template is preferably treated to denature or separate its strand(s) prior to amplification.

Preferably, the primer is an oligodeoxynucleotide and is sufficiently long to be used as a substrate for the synthesis of extension products by a nucleic acid polymerase. The appropriate primer length should take into account several factors, including temperature, structure of primer, and how the primer is used. For example, for diagnostic applications the oligonucleotide primer typically contains at least 15 nucleotides depending on the complexity of the target sequence. Other applications may require shorter oligonucleotide primers. It may be desirable to carry out these other application at cooler temperatures to form stable hybrid complexes with the template.

A nucleic acid polymerase as used in the invention refers to a chemical, physical, or biological agent which brings about the synthesis of either ribo- or deoxyribonucleotides into a nucleic acid polymer, or strand, in a template-dependent manner. Examples of nucleic acid polymerases include DNA polymerases. DNA polymerases bring about nucleic acid synthesis in a template-dependent manner in a 5' to 3' direction. Because of the complementarity between the template and the synthesized strand, this direction would be from a 3' region on the template to a 5' region on the template. The large fragment of DNA polymerase I from Bacillus stearothermophilus (Bst DNA polymerase I) lacking 5'–3' exonucleolytic activity is a preferred DNA polymerase. Other suitable DNA polymerases include Klenow polymerase and bacteriophage T7 DNA polymerase. The use of 5' blocked primers not susceptible to nucleolytic degradation should allow the use of DNA polymerases possessing 5'–3' exonucleolytic activity.

Complementary primers are selected to have a region complementary to the nucleic acid template. The primer sequence need not reflect the exact sequence of the template but must be able to hybridize with a template strand. Non-complementary bases can be interspersed into the primer provided the primer sequence has sufficient complementarity to hybridize with its corresponding sequence in the nucleic acid template such that the extension reaction can occur. The newly-formed extension product, once displaced, can act as a template for additional nucleic acid synthesis.

Preferably, the primers contain a non-complementary 5' region. Thus, the preferred primer contains a complementary region enabling it to hybridize to the nucleic acid template, and a non-complementary region. The presence of a non-complementary region has been found to enhance strand displacement.

The primer sequence can include one or more of the deoxyribonucleotide bases A, T, C, or G; and/or, one or more of the ribonucleotide bases A, U, C, or G and/or one or more modified nucleotide (deoxyribonucleotide or ribonucleotide) wherein the modification does not prevent hybridization of the primer to the nucleic acid, or elongation of the primer, or strand displacement.

Primers may be modified with chemical groups to enhance their performance or to facilitate the characterization of amplification products. For example, backbone-modified oligonucleotides such as phosphorothioates or methylphosphonates which are resistant to the nucleolytic activity of certain polymerases allow the use of such enzymes. Another example of modification involves using non-nucleotide linkers (e.g., Arnold et al., EPA 88 308 766-0) which do not interfere with elongation of the primer. Oligonucleotides containing mixtures of the desired modified and natural nucleotides may be used as well.

Primers may also contain reactive sites for enzymes such as restriction endonuclease cleavage sites or promotor sites for RNA polymerases. Examples of the use of such sites include cloning of amplification products and transcription of amplification products after amplification. Such sites are not necessary for amplification, but are helpful for subsequent manipulations of the amplified nucleic acids.

The primers of the present invention can be prepared by methods known in the art. Preferably, the primers are synthesized by chemical methods. For example, Caruthers et al., in: Methods In Enzymology, vol. 154, p. 287 (1987), describe using standard phosphoramidite solid-phase chemistry to join nucleotides by phosphodiester linkages. Bhatt, U.S. Pat. No 5,449,769 entitled "Method and reagent for sulfurization of organophosphorous compounds" filed Mar. 6, 1989, assigned to Gen-Probe Incorporated, the assignee of the present invention, describe a procedure for synthesizing oligonucleotides containing phosphorothioate linkages. Klem et al., entitled "Improved process for the synthesis of oligomers" PCT W092/07864, describe the synthesis of oligonucleotides having different linkages including methylphosphonate linkages. (These references are hereby incorporated by reference herein.) Automated synthesizers are well suited for oligonucleotide synthesis. In an automated synthesizer, one starts with a 5'-protected, immobilized (through the 3'-hydroxyl) nucleoside residue. After 5'-deprotection, a phosphite ester linkage is introduced by reaction with a 3'-phosphoramidite, 5'-protected nucleoside residue. The phosphite linkage is then oxidized to a stable linkage and the process is cycled with the desired nucleotide residues introduced into the synthesized sequence. The oxidative procedure can result in a typical phosphate ester or a phosphorothioate ester (Arnold et al., supra, EPA 88 308 766-0). Introduction of non-nucleotide phosphoramidite derivatives can be performed during automated synthesis. Also, the synthesized oligonucleotide can be further modified by synthetic methods (e.g., as described in U.S. Pat. No. 4,818,681).

The 5' end of the primer can be modified to be resistant to 5'-exonuclease activity present in nucleic acid polymerase. Such modifications can be carried out by adding a non-nucleotide group to the terminal 5' nucleotide of the primer using techniques such as those described by Arnold et al., U.S. Pat. No. 5,585,481, entitled "Linking Reagents for Nucleotide Probes," and the CLONTECH product catalogue describing the use of label-ON™ regents, hereby incorporated by reference herein.

Test Sample

In general any source of nucleic acid, in purified or non-purified form, can be utilized as the starting nucleic acid or acids provided it contains or is suspected of containing the target nucleic acid sequence. Depending on the source and purity of the nucleic acid, the starting nucleic acid may need to be purified prior to amplification. Purification of starting nucleic acid is preferably carried out when the nucleic acid source contains substances which inhibit amplification. Nucleic acid purification can be carried out using standard techniques.

The target sequence may be present in DNA or RNA, which may be single-stranded or double-stranded. A mixture of these nucleic acids or the nucleic acid from a previous amplification may also be utilized. The nucleic acid or mixture of nucleic acids may contain more than one target nucleic acid sequence which may be the same or different. The invention is therefore useful for simultaneously amplifying one or more different target nucleic acid sequences located on the same or different target nucleic acid strands.

The sample suspected or known to contain the intended target nucleic acid may be obtained from a variety of sources. Such sources include a biological sample; a food or agricultural sample; an environmental sample; body fluid or exudate such as urine, blood, milk, cerebrospinal fluid, sputum, saliva, stool, lung aspirates; and throat or genital swabs.

It may be desirable to treat the test samples to obtain nucleic acids suitable for amplification. For example, in certain circumstances, it is desirable to treat the test sample to release, extract, or denature, the target nucleic acid prior to amplification. Such treatments can remove impurities which inhibit amplification, and denature the nucleic acid to minimize the secondary structure (i.e., double-stranded DNA and hairpin loops) . These treatments can be carried out by means well known in the art.

Primers are designed to hybridize to specified regions of the target nucleic acid. Two sets of primers are preferably used. One set of primers, complementary primers, are designed to hybridize to a nucleic acid sequence present on the template nucleic acid 3' to the target sequence. Hybridization takes place based on hydrogen bonding between complementary nucleotides. The other set of primers, sense primers, are designed to be analogous to regions present on the template nucleic acid 5' to the target sequence. The members of each primer set are co-linearly arranged as shown diagrammatically in the FIGURE.

Both sets of primers are positioned such that the target sequence, present in the template and the complement to the template, will be amplified. DNA polymerases catalyze nucleic acid synthesis in a 5' to 3' direction (with respect to the template nucleotides are added from a 3' template region to a 5' template region). A complementary strand is produced from the initial template using the complementary primer. The complementary strand can act as a template for template-dependent nucleic acid synthesis.

If the sense primer is analogous to a region on the nucleic acid template 5' to the target sequence, it will be complementary to a region 3' to the target sequence on the complementary strand. The sense primer can act as a complementary primer with respect to the complementary strand. Template-dependent nucleic acid synthesis can then occur on the complementary strand thereby producing more target sequence.

Different numbers of complementary and sense primers may be used to amplify a target sequence. It appears that as the number of primers increases, amplification increases. Thus, the total number of complementary primers and sense primers is preferably more than 5. In preferred embodiments at least 4 sense primers and 4 complementary primers are used; at least 7 sense primers and 7 complementary primers are used; and at least 10 sense primers and 10 complementary primers are used. The number of complementary primers need not equal the number of sense primers. For example, a 2 sense primer and 3 complementary primer combination may be used.

When certain organic solvents such as DMSO are added to the amplification reaction and elevated temperature is used, substantial amplification as well as stringency is observed. If elevated temperature is used to increase strand displacement, a heat-stable nucleic acid polymerase such as a thermostable DNA polymerase may be employed. The temperature selected depends on the temperature range within which the enzyme is active.

The primers, nucleic acid polymerase, and nucleotides must be used in sufficient quantity to support the degree of amplification desired. Nucleotide analogs can be substituted or added provided the base pairing, DNA polymerase, and strand-displacing functions are not adversely affected to the point that the amplification does not proceed to the desired extent.

"Strand displacement" refers to the dissociation of a nucleic acid strand from its nucleic acid template in a 5' to 3' direction occurring due to template-directed nucleic acid synthesis by a nucleic acid polymerase. The newly synthesized and displaced nucleic acids have substantially the same nucleotide sequence which is complementary to the template nucleic acid sequence.

Preferably, a strand separation agent is used to enhance the strand displacement. Strand separation agents include enzymes such as helicases, the enzyme RecA which has helicase activity, and single-stranded nucleic acid binding protein. The use of helicases for separating strands of nucleic acid is described in Cold Spring Harbor Symposia on Quantitative Biology, Vol. XLIII, "DNA: Replication and Recombination" (New York: Cold Spring Harbor Laboratory, 1978) and the use of RecA is reviewed by Radding, Ann. Rev. Genetics, 16: 405 (1982). Strand separation is discussed by Kornberg, A, DNA Replication W. H. Freeman & Co., San Francisco, Calif., 1980. Zarling et al., U.S. Pat. No. 5,223,414 (Jun, 1993) discusses the use of RecA in nucleic acid hybridization and amplification.

Amplification, as discussed above, refers to increasing the number of target sequences. The degree of amplification can be increased by using conditions or agents which increase rates or extent of priming, or primer elongation. For example, a stand separation agent may increase the strand displacement rate of a DNA polymerase.

A wide variety of methods are available to detect a target sequence. For example, the nucleotide substrates or the primers can include a detectable label which is incorporated into newly synthesized DNA. The resulting labeled amplification product is then separated from the unused labeled nucleotides or primers and the label is detected in the separated product fraction.

Substances which serve as useful detectable labels are well known in the art and include radioactive isotopes (e.g., $^{32}$p, $^{3}$H, 1251, and $^{14}$C), fluorescent compounds, chemiluminescent compounds, chromophores, as well as ligands such as biotin and haptens which, while not directly detectable, can be readily detected by reaction with labeled forms of their specific binding partners, e.g., avidin and antibodies, respectively.

Another approach is to detect the amplification product by hybridization with a detectable nucleic acid probe and measuring the resulting hybrids in any conventional manner. In particular, the product can be assayed by hybridizing a chemiluminescent acridinium ester-labeled nucleic acid probe to the target sequence, selectively hydrolyzing the acridinium ester present on unhybridized probe, and measuring the chemiluminescence produced from the remaining acridinium ester in a luminometer. (See, e.g., Arnold et al., supra, PCT US88/02746, and Nelson et al., in Nonisotopic DNA Probe Techniques, p. 275 Academic Press, San Diego (Kricka, ed., 1992) (both references hereby incorporated by reference herein).

EXAMPLES

The present invention will now be illustrated, but is not intended to be limited, by the following examples.

Example 1

Amplification of an RNA Target

This example illustrates the amplification of a ribosomal RNA(rRNA) target sequence by producing a DNA template, and amplifying the DNA template using a primer array and a 5'-exo-minus DNA polymerase. Production of the DNA template from rRNA, and amplification of the template, was carried out in the same reaction vessel containing the necessary reagents for production and amplification of the DNA template.

The primer array used in this example comprised thirteen primers. The primers were prepared by standard phosphoramidite chemistry. Seven of the primers were complementary primers (with respect to the rRNA target). These primers had the following nucleic acid sequences (written 5' to 3'):

SEQ. ID. NO. 1: CGCGTCTAGT CCTACTCAGG TGTTG
SEQ. ID. NO. 2: CCCCAGATTC AGACTAGG
SEQ. ID. NO. 3: CGGTCATTGA CTAGTATTTA GCCTT
SEQ. ID. NO. 4: TTTCTTCATA GTACTGGTTC ACT
SEQ. ID. NO. 5: ATTTCACTCC CTTAACAAGG GTT
SEQ. ID. NO. 6: TTGTAAGCTA CAGGTTTCAG GT
SEQ. ID. NO. 7: ACGGGCAATT GGTCTGCGAC C

Six of the primers were sense primers (with respect to the rRNA target). These primers had the following nucleic acid sequences (written 5' to 3'):

SEQ. ID. NO. 8: AGCAAAGACC CGGAGGTCCG AAT
SEQ. ID. NO. 9: GAATACATAG GTATGCAAAG CGA
SEQ. ID. NO. 10: CCTGCCGAAC TGAAACATCT TAGT
SEQ. ID. NO. 11: CAGAGGAAAA GAAATCGAAG AGAT
SEQ. ID. NO. 12: TGTAGGATTG AGGATAAAGG AT
SEQ. ID. NO. 13: GGACTCCTAG TTGAACACAT CTG-GAAAGA

Target 23S rRNA was obtained from Chlamydia trachomatis (See, Glisin et al., Biochemistry 13:2633 (1974)), and diluted in buffer (50 mM Tris-HCl (PH 8.3), 37.5 mM KCl, 1.5 mM $MgCl_2$, 10 mM DTT) . Variable amounts of rRNA target were combined with primers ($7\times10^{-12}$ mole) in 20 $\mu$l of buffer (7% DMSO, 50 mM Tris-HCl (pH 8.3) 75 mM KCl, 3 mM $MgCl_2$, and 2 mM DTT) and incubated at 60° C. for 30 minutes to pre-hybridize the primers. The pre-hybridized primers were then treated with 0.2 mM ATP, 0.2 mM TTP, 0.2 mM GTP, 0.2 mM CTP, 200 units of Maloney Murine Leukemia Virus reverse transcriptase (MMLV-RT), and 2 units of Bst DNA polymerase 1. Amplification was carried out at 37° C. for 60 minutes, then at 60° C. for 120 minutes.

The amplification products were then denatured and assayed using acridinium ester labeled probe according to Nelson et al., supra. Denaturation was carried out by incubating at 95° C. for 5 minutes. Probe labeling with acridinium ester was carried out as described by Nelson et al., supra. The acridinium ester labeled probe was synthesized to have the nucleic acid sequence corresponding to SEQ. ID. NO. 27. The acridinium ester labeled probe ($2\times10^{-11}$ moles) was incubated with amplified product at 60°60 C. for 15 minutes in 100 $\mu$l of hybridization buffer (100 mM lithium succinate (pH 5.2), 8% lithium dodecyl sulfate, 1.5 mM EDTA, and 1.5 mM EGTA). The acridinium ester present on unhybridized probe was then hydrolyzed by adding a reagent solution (0.15 M sodium tetraborate, pH 7.6, and 5% (v/v) Triton X-100) and incubating at 60° C. for 10 minutes. The remaining chemiluminescence was measured in a luminometer. The results shown in Table 1 demonstrate a titration of the target nucleic acid in the amplification method of the present invention.

TABLE 1

| Chlamydia rRNA (Moles) | RLU (mean) |
|---|---|
| $4\times10^{-18}$ | 307893 |
| $4\times10^{-19}$ | 54771 |
| $4\times10^{-20}$ | 3644 |
| $4\times10^{-23}$ | 2354 |
| 0 | 2307 |

Example 2

Amplification of a Clinical Specimen

This example illustrates the amplification of an rRNA target sequence present in a clinical sample (cervical swab sample). The oligonucleotides, amplification procedure, and detection procedure used in this example were as described in Example 1. This example differs from Example 1 in the type of sample used, and sample preparation.

Cervical swab samples were collected and suspended in a buffered solution containing an anionic detergent (60 mM phosphate buffer (pH 6.8), 6% lithium dodecyl sulfate, 2 mM EDTA, and 2 mM EGTA). The clinical specimen was spiked with 10–18 moles of 23S Chamydia trachomatis rRNA, hybridized with the primers, amplified, and detected, as described in Example 1. A successful amplification of target nucleic acid in the clinical sample was indicated by the clinical sample with Chlamydia rRNA having an RLU over 50 fold greater than a clinical sample without Chlamydia rRNA.

Example 3

Specificity of Amplification

This example illustrates the amplification of a specific target sequence using probes directed to a target sequence and a non-target sequence (i.e., a region of the transcript outside the amplicon). The target nucleic acid used in this example was derived from gene 10 of 17 bacteriophage. In particular, an XmaI and BanI digest of pGEMX1 containing part of gene 10 of T7 bacteriophage was sub-cloned into pUC19. Expression of the insert with T7 RNA polymerase yielded an RNA product 863 bases in length and this transcript was used to produce a DNA template which was then amplified.

The primer array, used to amplify the target sequence, was made up of four complementary primers (with respect to the RNA transcript) having the following nucleic acid sequences (written 5' to 31'):

SEQ. ID. NO. 14 CTATAGGGAG ACCACAACGG TTT
SEQ. ID. NO. 15 CTAGAAATAA TTTTGTTTAA CTT
SEQ. ID. NO. 16 AGAAGGAGAT ATACATATGG CT
SEQ. ID. NO. 17 CATGACTGGT GGACAGCAAA TG and four primers having the same sense as the RNA transcript, having the following nucleic acid sequences (written 5' to 3'):

SEQ. ID. NO. 18 GAGCGAACGC AGTCAGGA
SEQ. ID. NO. 19 GAGAAGTGGT CACGGAGGTA CGAGCGAACG CAGT
SEQ. ID. NO. 20 GGAGATGGAA CGTACCATGT
SEQ. ID. NO. 21 GGGAACTGAG CGGATTTACC GC

Hybridization, amplification, and detection were carried out as described in Example 1. Acridinium ester-labeled probes, SEQ. ID. NO: 22 and SEQ. ID. NO. 27 were used to detect the presence of the target sequence. A non-target acridinium ester labeled probe (SEQ. ID. NO. 23) was used as a control to determine non-specific amplification occurring outside the primer region (e.g., 3' of the complementary primers and 5' the sense primers) . The results shown in Table 2 demonstrate that the amplification is specific.

TABLE 2

| Probe | Sample | RLU (mean) |
|---|---|---|
| SEQ. ID. 22 + SEQ. ID. 27 | ($4\times10^{-19}$ mole) | 240474 |
| SEQ. ID. 23 | ($4\times10^{-19}$ mole) | 3091 |
| SEQ. ID. 23 | no target | 2720 |

Example 4

Enhanced Strand Displacement

This example demonstrates the ability of a non-complementary region, attached to a primer, to enhance strand displacement and amplification. Strand displacement was measured using two different combinations of complementary primers. Both combinations contained a 5'-$^{32}$p labeled primer (SEQ. ID. NO. 19) and an additional primer. The additional primer in one combination corresponded to SEQ. ID. NO. 24. The additional primer in the other combination corresponded to SEQ. ID. NO. 25. The SEQ. ID. NO. 25 primer was similar to the SEQ. ID. NO. 24 primer, but had five fewer complementary nucleotides and contained a 5' non-complementary region. Amplification was carried out on an oligodeoxynucleotide template corresponding to a portion of the T7 bacteriophage gene 10. The template, corresponding to SEQ. ID. NO: 26, was synthesized as described in Example 1.

The primers 4'$10^{-32}$ mole) were prehybridized with template ($4\times10^{-13}$ mole) in 20 $\mu$l of buffer (50 mM Tris-HCl (PH 8.3), 37.5 mM KCl, 1.5 MM $MgCl_2$, 10 mM DTT), by incubating at 70° C. for 5 minutes, and the reaction was then allowed to cool to room temperature (about 20–25° C.) over the course of about 2 hours. Amplification was carried out by adding 0.1 mM ATP, 0.1 mM TTP, 0.1 mM GTP, 0.1 mM CTP, 4 units Bst DNA polymerase I and incubating at 50° C. Time points were taken at 5, 15, and 30 minutes by transferring aliquots of the reaction to a formamide/EDTA solution (50% formamide 10 mM Tris-HCl pH 8.0, 0.1 mM EDTA). The samples were loaded and run on a denaturing 15% polyacrylamide gel. Bands corresponding to the elongation product and primer were excised from the gel and analyzed by Cerenkov counting in a scintillation counter.

The results shown in Table 3 demonstrate that strand displacement is more efficient using primers with a 5' non-complementary region. The "% product" refers to the amount of elongation product divided by the sum of the amount of elongation product and primer. The higher percentage of product observed with the primer having a 5' non-complementary region indicates increased amplification and strand displacement.

TABLE 3

| Primer (SEQ. ID. NO)[1] | 24 | 24 | 24 | 25 | 25 | 25 |
|---|---|---|---|---|---|---|
| Time | 5 min | 15 min | 30 min | 5 min | 15 min | 30 min |
| % Product | 4.3 | 5.8 | 5.9 | 18 | 25 | 35 |

[1]In addition to the primers listed in Table 4, each reaction mixture contained a radiolabeled primer having the nucleotide sequence of SEQ. ID. NO. 19.

The present embodiments of this invention are to be considered in all respects as illustrative and not restrictive, the scope of the invention being indicated by the appended claims rather than by the foregoing description, and all changes which come within the meaning and range of equivalency of the claims therefore are intended to be embraced therein.

Other embodiments are within the following claims.

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
(A) LENGTH: 25
(B) TYPE: nucleic acid
(C) STRANDEDNESS: single
(D) TOPOLOGY: linear (xi) SEQUENCE DESCRIPTION: SEQ ID NO: 1:

CGCGTCTAGT CCTACTCAGG TGTTG 25

(2) INFORMATION FOR SEQ ID NO: 2:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO: 2:

CCCCAGATTC AGACTAGG 18

(2) INFORMATION FOR SEQ ID NO: 3:

(i) SEQUENCE CHARACTERISTICS:
(A) LENGTH: 25
(B) TYPE: nucleic acid
(C) STRANDEDNESS: single
(D) TOPOLOGY: linear (xi) SEQUENCE DESCRIPTION: SEQ ID NO: 3:

CGGTCATTGA CTAGTATTTA GCCTT 25

(2) INFORMATION FOR SEQ ID NO: 4:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO: 4:

TTTCTTCATA GTACTGGTTC ACT 23

(2) INFORMATION FOR SEQ ID NO: 5:

(i) SEQUENCE CHARACTERISTICS:

-continued (A) LENGTH: 23
(B) TYPE: nucleic acid
(C) STRANDEDNESS: single
(D) TOPOLOGY: linear (xi) SEQUENCE DESCRIPTION: SEQ ID NO: 5:

ATTTCACTCC CTTAACAAGG GTT 23

(2) INFORMATION FOR SEQ ID NO: 6:

(i) SEQUENCE CHARACTERISTICS:
(A) LENGTH: 22
(B) TYPE: nucleic acid
(C) STRANDEDNESS: single
(D) TOPOLOGY: linear (xi) SEQUENCE DESCRIPTION: SEQ ID NO: 6:

TTGTAAGCTA CAGGTTTCAG GT 22

(2) INFORMATION FOR SEQ ID NO: 7:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 7:

ACGGGCAATT GGTCTGCGAC C 21

(2) INFORMATION FOR SEQ ID NO: 8:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO: 8:

AGCAAAGACC CGGAGGTCCG AAT 23

(2) INFORMATION FOR SEQ ID NO: 9:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO: 9:

GAATACATAG GTATGCAAAG CGA 23

(2) INFORMATION FOR SEQ ID NO: 10:

(i) SEQUENCE CHARACTERISTICS:
(A) LENGTH: 24
(B) TYPE: nucleic acid
(C) STRANDEDNESS: single
(D) TOPOLOGY: linear (xi) SEQUENCE DESCRIPTION: SEQ ID NO: 10:

CCTGCCGAAC TGAAACATCT TAGT 24

(2) INFORMATION FOR SEQ ID NO: 11:

(i) SEQUENCE CHARACTERISTICS:
(A) LENGTH: 24

-continued (B) TYPE: nucleic acid
(C) STRANDEDNESS: single
(D) TOPOLOGY: linear (xi) SEQUENCE DESCRIPTION: SEQ ID NO: 11:

CAGAGGAAAA GAAATCGAAG AGAT 24

(2) INFORMATION FOR SEQ ID NO: 12:

(i) SEQUENCE CHARACTERISTICS:
(A) LENGTH: 22
(B) TYPE: nucleic acid
(C) STRANDEDNESS: single
(D) TOPOLOGY: linear (xi) SEQUENCE DESCRIPTION: SEQ ID NO: 12:

TGTAGGATTG AGGATAAAGG AT 22

(2) INFORMATION FOR SEQ ID NO: 13:

(i) SEQUENCE CHARACTERISTICS:
(A) LENGTH: 29
(B) TYPE: nucleic acid
(C) STRANDEDNESS: single
(D) TOPOLOGY: linear (xi) SEQUENCE DESCRIPTION: SEQ ID NO: 13:

GGACTCCTAG TTGAACACAT CTGGAAAGA 29

(2) INFORMATION FOR SEQ ID NO: 14:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO: 14:

CTATAGGGAG ACCACAACGG TTT 23

(2) INFORMATION FOR SEQ ID NO: 15:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO: 15:

CTAGAAATAA TTTTGTTTAA CTT 23

(2) INFORMATION FOR SEQ ID NO: 16:

(i) SEQUENCE CHARACTERISTICS:
(A) LENGTH: 22
(B) TYPE: nucleic acid
(C) STRANDEDNESS: single
(D) TOPOLOGY: linear (xi) SEQUENCE DESCRIPTION: SEQ ID NO: 16:

AGAAGGAGAT ATACATATGG CT 22

(2) INFORMATION FOR SEQ ID NO: 17:

(i) SEQUENCE CHARACTERISTICS:
(A) LENGTH: 22
(B) TYPE: nucleic acid

-continued (C) STRANDEDNESS: single
(D) TOPOLOGY: linear (xi) SEQUENCE DESCRIPTION: SEQ ID NO: 17:

CATGACTGGT GGACAGCAAA TG 22

(2) INFORMATION FOR SEQ ID NO: 18:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO: 18:

GAGCGAACGC AGTCAGGA 18

(2) INFORMATION FOR SEQ ID NO: 19:

(i) SEQUENCE CHARACTERISTICS:
(A) LENGTH: 34
(B) TYPE: nucleic acid
(C) STRANDEDNESS: single
(D) TOPOLOGY: linear (xi) SEQUENCE DESCRIPTION: SEQ ID NO: 19:

GAGAAGTGGT CACGGAGGTA CGAGCGAACG CAGT 34

(2) INFORMATION FOR SEQ ID NO: 20:

(i) SEQUENCE CHARACTERISTICS:
(A) LENGTH: 20
(B) TYPE: nucleic acid
(C) STRANDEDNESS: single
(D) TOPOLOGY: linear (xi) SEQUENCE DESCRIPTION: SEQ ID NO: 20:

GGAGATGGAA CGTACCATGT 20

(2) INFORMATION FOR SEQ ID NO: 21:

(i) SEQUENCE CHARACTERISTICS:
(A) LENGTH: 22
(B) TYPE: nucleic acid
(C) STRANDEDNESS: single
(D) TOPOLOGY: linear (xi) SEQUENCE DESCRIPTION: SEQ ID NO: 21:

GGGAACTGAG CGGATTTACC GC 22

(2) INFORMATION FOR SEQ ID NO: 22:

(i) SEQUENCE CHARACTERISTICS:
(A) LENGTH: 27
(B) TYPE: nucleic acid
(C) STRANDEDNESS: single
(D) TOPOLOGY: linear (xi) SEQUENCE DESCRIPTION: SEQ ID NO: 22:

GAACAACGCC AGTTTGATCT CCAGCAG 27

(2) INFORMATION FOR SEQ ID NO: 23:

(i) SEQUENCE CHARACTERISTICS:
(A) LENGTH: 26
(B) TYPE: nucleic acid
(C) STRANDEDNESS: single -continued

```
          (D) TOPOLOGY: linear

    (xi) SEQUENCE DESCRIPTION: SEQ ID NO: 23:

CAACCTCAAA GGCCCATAAC GTTGCG                                        26


(2) INFORMATION FOR SEQ ID NO: 24:

     (i) SEQUENCE CHARACTERISTICS:
          (A) LENGTH: 29
          (B) TYPE: nucleic acid
          (C) STRANDEDNESS: single
          (D) TOPOLOGY: linear

    (xi) SEQUENCE DESCRIPTION: SEQ ID NO: 24:

GTCAGGACTT CACCGCCAAA TACCTTCAA                                     29


(2) INFORMATION FOR SEQ ID NO: 25:

     (i) SEQUENCE CHARACTERISTICS:
          (A) LENGTH: 50
          (B) TYPE: nucleic acid
          (C) STRANDEDNESS: single
          (D) TOPOLOGY: linear

    (xi) SEQUENCE DESCRIPTION: SEQ ID NO: 25:

GAAATTAATA CGACTCACTA TAGGGAGACT TCACCGCCAA ATACCTTCAA              50


(2) INFORMATION FOR SEQ ID NO: 26:

     (i) SEQUENCE CHARACTERISTICS:
          (A) LENGTH: 137
          (B) TYPE: nucleic acid
          (C) STRANDEDNESS: single
          (D) TOPOLOGY: linear

    (xi) SEQUENCE DESCRIPTION: SEQ ID NO: 26:

CATGACTGGT GGACAGCAAA TGGGTACTAA CCAAGGTAAA GGTGTAGTTG              50

CTGCTGGAGA TAAACTGGCG TTGTTCTTGA AGGTATTTGG CGGTGAAGTC             100

CTGACTGCGT TCGCTCGTAC CTCCGTGACC ACTTCTC                           137


(2) INFORMATION FOR SEQ ID NO: 27:

     (i) SEQUENCE CHARACTERISTICS:
          (A) LENGTH: 27
          (B) TYPE: nucleic acid
          (C) STRANDEDNESS: single
          (D) TOPOLOGY: linear

    (xi) SEQUENCE DESCRIPTION: SEQ ID NO: 27:

CCCGTAGACG AAAGGAGAGA AAGACCG                                       27
```

What is claimed is:

1. A method for amplifying a specific nucleic acid target sequence preferentially over non-target sequences, comprising the steps of:

contacting a nucleic acid strand containing said target sequence with a nucleic acid polymerase lacking 5' exonuclease activity, at least one nucleotide triphosphate selected from adenosine, thymidine, guanosine and cytidine triphosphate, and at least three different complementary primers under primer extension conditions at essentially constant temperature, wherein each said primer contains a nucleotide base sequence which is designed to be complementary to a nucleic acid sequence on said nucleic acid strand located 3' to said target sequence, and wherein said nucleotide base sequence of each said primer is able to hybridize to a nucleic acid sequence on said nucleic acid strand under said conditions; and amplifying said target sequence, *wherein said amplifying step is performed in the absence of a complementary or sense primer containing a promoter site for an RNA polymerase.*

2. A method for amplifying a specific nucleic acid target sequence preferentially over non-target sequences, comprising the steps of:

contacting a nucleic acid strand containing said target sequence with a nucleic acid polymerase lacking 5' exonuclease activity, at least one nucleotide triphosphate selected from adenosine, thymidine, guanosine and cytidine triphosphate, and at least two different complementary primers, under primer extension conditions at essentially constant temperature, wherein each said primer contains a nucleotide base sequence which is designed to be complementary to a nucleic acid sequence on said nucleic acid strand located 3' to said target sequence, and wherein said nucleotide base sequence of each said primer is able to hybridize to a nucleic acid sequence on said nucleic acid strand under said conditions; and amplifying said target sequence in the absence of any restriction endonuclease active on a product of said amplification, *wherein said amplifying step is performed in the absence of a complementary or sense primer containing a promoter site for an RNA polymerase.*

3. A method for amplifying a specific nucleic acid target sequence preferentially over non-target sequences, comprising the steps of:

contacting a nucleic acid strand containing said target sequence with a nucleic acid polymerase, at least one nucleotide triphosphate selected from adenosine, thymidine, guanosine and cytidine triphosphate, and at least three different complementary primers, under primer extension conditions at essentially constant temperature, wherein each said primer contains a nucleotide base sequence which is designed to be complementary to a nucleic acid sequence on said nucleic acid strand located 3' to said target sequence, and wherein said nucleotide base sequence of each said primer is able to hybridize to a nucleic acid sequence on said nucleic acid strand under said conditions, and wherein at least one of said primers is modified to be resistant to nucleolytic degradation by a 5'-exonuclease; and amplifying said target sequence, *wherein said amplifying step is performed in the absence of a complementary or sense primer containing a promoter site for an RNA polymerase.*

4. A method for amplifying a specific nucleic acid target sequence preferentially over non-target sequences, comprising the steps of:

contacting a nucleic acid strand containing said target sequence with a nucleic acid polymerase, at least one nucleotide triphosphate selected from adenosine, thymidine, guanosine and cytidine triphosphate, and at least two different complementary primers, under primer extension conditions at essentially constant temperature, wherein each said primer contains a nucleotide base sequence which is designed to be complementary to a nucleic acid sequence on said nucleic acid strand located 3' to said target sequence, and wherein said nucleotide base sequence of each said primer is able to hybridize to a nucleic acid sequence on said nucleic acid strand under said conditions, and wherein at least one of said primers is modified to be resistant to nucleolytic degradation by a 5'-exonuclease; and amplifying said target sequence in the absence of any restriction endonuclease active on a product of said amplification, *wherein said amplifying step is performed in the absence of a complementary or sense primer containing a promoter site for an RNA polymerase.*

5. The method of claim 1, wherein at least four said complementary primers are used.

6. The method of claim 2, wherein at least four said complementary primers are used.

7. The method of claim 5, wherein each of said complementary primers is separated by a distance of 1 to 200 nucleotides.

8. The method of claim 6, wherein each of said complementary primers is separated by a distance of 1 to 200 nucleotides.

9. A method for exponentially amplifying a specific nucleic acid target sequence preferentially over non-target sequences, comprising the steps of:

contacting a nucleic acid strand containing said target sequence with a nucleic acid polymerase lacking 5' exonuclease activity, at least one nucleotide triphosphate selected from adenosine, thymidine, guanosine and cytidine triphosphate, and a primer array of at least five different primers comprising two or three different complementary primers and two or three different sense primers, under [oligonucleotide] primer extension conditions at essentially constant temperature, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence of said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and exponentially amplifying said target sequence in the absence of any restriction endonuclease active on a product of said amplification, *wherein said amplifying step is performed in the absence of a complementary or sense primer containing a promoter site for an RNA polymerase.*

10. A method for amplifying a specific nucleic acid target sequence preferentially over non-target sequences, comprising the steps of:

contacting a nucleic acid strand containing said target sequence with a nucleic acid polymerase, at least one-nucleotide triphosphate selected from adenosine, thymidine, guanosine and cytidine triphosphate, and a primer array of at least five different primers comprising two or three different complementary primers and two or three different sense primers, under primer extension conditions at essentially constant temperature, wherein at least one of said primers is modified to be resistant to nucleolytic degradation by a 5' exonuclease, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid complementary to a nucleic acid sequence on said nucleic acid strand under said conditions; and amplifying said target sequence, *wherein said amplifying step is performed in the absence of a complementary or sense primer containing a promoter site for an RNA polymerase.*

11. A method for exponentially amplifying a specific DNA target sequence preferentially over non-target sequences, comprising the steps of:

contacting a single stranded DNA containing said target sequence with a DNA polymerase lacking 5' exonuclease activity, at least one nucleotide triphosphate selected from adenosine, thymidine, guanosine and cytidine triphosphate, and a primer array of at least five different primers comprising two or three different complementary primers and two or three different sense primers, under primer extension conditions at essentially constant temperature, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and exponentially amplifying said target sequence in the absence of any restriction endonuclease active on a product of said amplification, *wherein said amplifying step is performed in the absence of a complementary or sense primer containing a promoter site for an RNA polymerase.*

12. A method for amplifying a specific DNA target sequence preferentially over non-target sequences, comprising the steps of:

contacting a single stranded DNA containing said target sequence with a DNA polymerase, at least one nucleotide triphosphate selected from adenosine, thymidine, guanosine and cytidine triphosphate, and a primer array of at least five different primers comprising two to three different complementary primers and two to three different sense primers, under primer extension conditions at essentially constant temperature, wherein at least one of said primers is modified to be resistant to nucleolytic degradation by a 5' exonuclease, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and amplifying said target sequence, *wherein said amplifying step is performed in the absence of a complementary or sense primer containing a promoter site for an RNA polymerase.*

13. The method of claim 9, wherein at least 4 said sense primers and at least 4 said complementary primers are used.

14. The method of claim 9, wherein at least 7 said sense primers and at least 7 said complementary primers are used.

15. The method of claim 9, wherein at least 10 said sense primers and at least 10 said complementary primers are used.

16. The method of claim 9, wherein each adjacent said sense primer is separated by a distance of 1 to 200 nucleotides, and each adjacent said complementary primer is separated by a distance of 1 to 200 nucleotides.

17. The method of claim 13, wherein each adjacent said sense primer is separated by a distance of 1 to 200 nucleotides, and each adjacent said complementary primer is separated by a distance of 1 to 200 nucleotides.

18. The method of claim 14, wherein each adjacent said sense primer is separated by a distance of 1 to 200 nucleotides, and each adjacent said complementary primer is separated by a distance of 1 to 200 nucleotides.

19. The method of claim 15, wherein each adjacent said sense primer is separated by a distance of 1 to 200 nucleotides, and each adjacent said complementary primer is separated by a distance of 1 to 200 nucleotides.

20. The method of claim 16, wherein two adjacent sense primers are separated by a distance of up to 10 nucleotides, and two adjacent complementary primer are separated by a distance of up to 10 nucleotides.

21. A method for exponentially amplifying a specific nucleic acid target sequence preferentially over non-target sequences, comprising the steps of:

contacting a nucleic acid strand containing said target sequence with a nucleic acid polymerase lacking 5' exonuclease activity, at least one nucleotide triphosphate selected from adenosine, thymidine, guanosine and cytidine triphosphate, and at least two different complementary primers and at lease two different sense primers under primer extension conditions at essentially constant temperature, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and exponentially amplifying said target sequence in the absence of any restriction endonuclease active on a product of said amplification, *wherein said amplifying step is performed in the absence of a complementary or sense primer containing a promoter site for an RNA polymerase.*

22. A method for amplifying a specific nucleic acid target sequence preferentially over non-target sequences, comprising the steps of:

contacting a nucleic acid strand containing said target sequence with a nucleic acid polymerase, at least one nucleotide triphosphate selected from adenosine, thymidine, guanosine and cytidine triphosphate, and at least two different complementary primers and at least two different sense primers under primer extension conditions at essentially constant temperature, wherein at least one of said primers is modified to be resistant to nucleolytic degradation by a 5'-exonuclease, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and amplifying said target sequence in the absence of any restriction endonuclease active on a product of said amplification, *wherein said amplifying step is performed in the absence of a complementary or sense primer containing a promoter site for an RNA polymerase.*

23. A method for exponentially amplifying a specific DNA target sequence preferentially over non-target sequences, comprising the steps of:

contacting a single stranded DNA containing said target sequence with a DNA polymerase lacking 5' exonuclease activity, at least one nucleotide triphosphate selected from adenosine, thymidine, guanosine and cytidine triphosphate, at lease two different complementary primers and at least two different sense primers under primer extension conditions at essentially constant temperature, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and exponentially amplifying said target sequence in the absence of any restriction endonuclease active on a product of said amplification, *wherein said amplifying step is performed in the absence of a primer containing a promoter site for an RNA polymerase.*

24. A method for amplifying a specific DNA target sequence preferentially over non-target sequences, comprising the steps of:

contacting a single stranded DNA containing said target sequence with a DNA polymerase, at least one nucleotide triphosphate selected from adenosine, thymidine, guanosine and cytidine triphosphate, at least two different complementary primers and at least two different sense primers under primer extension conditions at essentially constant temperature, wherein at least one of said primers is modified to be resistant to nucleolytic degradation by a 5' -exonuclease, wherein each said complementary primer contains a nucleotide base sequence which is designed to be complementary to a nucleic acid sequence on said nucleic acid strand located 3' to said target sequence, and wherein said nucleotide base sequence of each said complementary primer is able to hybridize to a nucleic acid sequence on said nucleic acid strand under said conditions, wherein each said sense primer contains a nucleotide base sequence which is designed to be analogous to a nucleic acid sequence on said nucleic acid strand located 5' to said target sequence, and wherein said nucleotide base sequence of each said sense primer is able to hybridize to a nucleic acid sequence complementary to a nucleic acid sequence on said nucleic acid strand under said conditions; and amplifying said target sequence in the absence of any restriction endonuclease active on a product of said amplification, *wherein said amplifying step is performed in the absence of a complementary or sense primer containing a promoter site for an RNA polymerase.*

25. The method of claim 23, wherein said conditions include provision of DMSO.

26. The method of claim 23, wherein said essentially constant temperature is at least 43° C.

27. The method of claim 26, wherein said essentially constant temperature is between 60° C. and 70° C.

28. The method of claim 23, wherein said conditions include provision of a strand-displacing agent.

29. The method of claim 28, wherein said strand-displacing agent is selected from the group consisting of a helicase, a RecA protein, and a single-stranded nucleic acid binding protein.

30. The method of claim 23, wherein said DNA polymerase is Bst DNA polymerase I or a modified Taq DNA polymerase.

31. The method of claim 23, wherein at least one of the oligonucleotide primers further comprises a 5' non-complementary region.

32. The method of claim 23, wherein at least 4 said complementary primers, and at least 4 said sense primers, are used.

33. The method of claim 23, wherein at least 7 said complementary primers, and at least 7 said sense primers, are used.

34. The method of claim 23, wherein at least 10 said sense primers, and at least 10 said complementary primers, are used.

35. The method of claim 10, wherein at least one said sense primer and one said complementary primer are modified to be resistant to nucleolytic degradation by any 5'-exonuclease present in said contacting step.

36. The method of claim 12, wherein at least one said sense primer and one said complementary primer are modified to be resistant to nucleolytic degradation by any 5'-exonuclease present in said contacting step.

37. The method of claim 22, wherein at least one said sense primer and one said complementary primer are modified to be resistant to nucleolytic degradation by any 5'-exonuclease present in said contacting step.

38. The method of claim 24, wherein at least one said sense primer and one said complementary primer are modified to be resistant to nucleolytic degradation by any 5'-exonuclease present in said contacting step.

39. The method of claim 10, wherein said amplifying step is an exponential amplification.

40. The method of claim 12, wherein said amplifying step is an exponential amplificatiion.

41. The method of claim 22, wherein said amplifying step is an exponential amplification.

42. The method of claim 24, wherein said amplifying step is an exponential amplification.

* * * * *